(12) United States Patent
Feldchtein

(10) Patent No.: US 8,600,334 B2
(45) Date of Patent: Dec. 3, 2013

(54) PATIENT LEAKAGE CURRENT LIMITATION

(75) Inventor: Mikhael Feldchtein, Qiriat Yam (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 48 days.

(21) Appl. No.: 13/181,875

(22) Filed: Jul. 13, 2011

(65) Prior Publication Data

US 2013/0017799 A1    Jan. 17, 2013

(51) Int. Cl.
    *H04B 1/16*    (2006.01)
(52) U.S. Cl.
    USPC ............ 455/337; 600/300; 600/323; 324/307
(58) Field of Classification Search
    USPC .......................................................... 455/337
    See application file for complete search history.

(56) References Cited

U.S. PATENT DOCUMENTS

| | | | |
|---|---|---|---|
| 3,465,103 A | 9/1969 | Lynch | |
| 3,922,686 A | 11/1975 | France et al. | |
| 4,106,494 A * | 8/1978 | McEachern | 600/508 |
| 5,267,150 A * | 11/1993 | Wilkinson | 600/509 |
| 5,800,432 A * | 9/1998 | Swanson | 606/49 |
| 6,711,440 B2 * | 3/2004 | Deal et al. | 607/9 |
| 7,072,390 B1 * | 7/2006 | Sorrells et al. | 375/222 |
| 2004/0116094 A1 | 6/2004 | Eastwood | |
| 2006/0089541 A1 | 4/2006 | Braun et al. | |
| 2007/0173701 A1 * | 7/2007 | Al-Ali | 600/300 |
| 2007/0213625 A1 | 9/2007 | Nayak et al. | |
| 2010/0001725 A1 * | 1/2010 | Van Liere | 324/307 |

FOREIGN PATENT DOCUMENTS

DE        2 328 834        12/1973

OTHER PUBLICATIONS

Extended European Search Report dated Oct. 19, 2012 received from related European Application No. 12176091.2.

* cited by examiner

*Primary Examiner* — Ajibola Akinyemi
(74) *Attorney, Agent, or Firm* — Louis J. Capezzuto, Esq.

(57) ABSTRACT

A baseband receiver, consisting of a receiver input port, configured to receive a baseband signal generated in response to electrical activity in tissue of a human patient. The receiver includes a modulator, configured to modulate a local oscillator signal with the baseband signal, and an isolating device configured to receive the modulated local oscillator signal at an input port of the device and in response to generate a modulated output local oscillator signal at an output port of the device. The receiver further includes a demodulator configured to demodulate the modulated output local oscillator signal with the local oscillator signal so as to recover the baseband signal.

30 Claims, 8 Drawing Sheets

PATIENT LEAKAGE CURRENT LIMITATION

FIELD OF THE INVENTION

The present invention relates generally to leakage current that is present during a medical procedure, and specifically to limiting the possible leakage current to an acceptable level.

BACKGROUND OF THE INVENTION

During medical procedures, especially procedures performed on the heart of a patient, it is critical to ensure that no inadvertent current passes through the patient. Such currents, typically caused by leakage from equipment that may be connected directly or indirectly to the patient, may have catastrophic results. Any system that reduces possible leakage currents through a patient also reduces the chance of a catastrophic incident.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a baseband receiver, including:

a receiver input port, configured to receive a baseband signal generated in response to electrical activity in tissue of a human patient;

a modulator, configured to modulate a local oscillator signal with the baseband signal;

an isolating device configured to receive the modulated local oscillator signal at an input port of the device and in response to generate a modulated output local oscillator signal at an output port of the device; and a demodulator configured to demodulate the modulated output local oscillator signal with the local oscillator signal so as to recover the baseband signal.

Typically, the isolating device includes a transformer having a primary coil galvanically insulated from a secondary coil.

Alternatively, the isolating device includes an optoelectronic converter having an input port galvanically insulated from an output port. An analog to digital converter (ADC) may be coupled to the input port, and a digital to analog converter (DAC) may be coupled to the output port, and the ADC and the DAC may be connected to the optoelectronic converter.

The receiver may include a local oscillator configured to generate the local oscillator signal. Typically, the received baseband signal is referenced to an input reference rail, and the local oscillator signal modulated by the modulator is referenced to the input reference rail. The local oscillator signal may be input to the demodulator, and may be referenced to an output reference rail, and the recovered baseband signal may be referenced to the output reference rail.

In a disclosed embodiment the receiver includes an isolating transformer configured to electrically insulate the local oscillator signal input to the modulator from the local oscillator signal input to the demodulator.

In a further disclosed embodiment the receiver includes a low pass filter coupled to the demodulator and configured to reject frequencies higher than baseband frequencies.

In a yet further disclosed embodiment the receiver includes a processor configured to store a parameter relating the baseband signal received at the receiver input port with the recovered baseband signal from the demodulator.

An alternative embodiment includes a receiver output port configured to receive the recovered baseband signal from the demodulator, and to provide the recovered baseband signal to a module configured to perform at least one of an electrical signal transmission to the human patient and an electrical signal reception from the human patient. Typically, the module includes a tracker module configured to receive tracking signals from the human patient so as to track a probe within the patient. Alternatively or additionally, the module includes an ablation module configured to transmit ablation power to the human patient so as to ablate the tissue.

A further alternative embodiment includes an electronic device coupled to the demodulator and configured to reject a direct current (DC) level.

There is further provided, according to an embodiment of the present invention, a baseband receiver, including:

an isolating device configured to receive a local oscillator signal modulated by a baseband signal, generated in response to electrical activity in tissue of a human patient, at an input port of the device and in response to generate a modulated output local oscillator signal at an output port of the device; and a demodulator configured to demodulate the modulated output local oscillator signal with the local oscillator signal so as to recover the baseband signal.

Typically, the isolating device includes a transformer having a primary coil galvanically insulated from a secondary coil.

The receiver may include an ablation module configured to transmit ablation power to the human patient at an ablation frequency, the module including a local oscillator configured to provide the local oscillator signal to the demodulator at the ablation frequency.

There is further provided, according to an embodiment of the present invention a method, including:

receiving a baseband signal generated in response to electrical activity in tissue of a human patient;

modulating a local oscillator signal with the baseband signal;

receiving the modulated local oscillator signal at an input port of an isolating device and in response generating a modulated output local oscillator signal at an output port of the device; and demodulating the modulated output local oscillator signal with the local oscillator signal so as to recover the baseband signal.

There is further provided, according to an embodiment of the present invention a method, including:

receiving a local oscillator signal modulated by a baseband signal, generated in response to electrical activity in tissue of a human patient, at an input port of an isolating device and in response generating a modulated output local oscillator signal at an output port of the device; and demodulating the modulated output local oscillator signal with the local oscillator signal so as to recover the baseband signal.

The present disclosure will be more fully understood from the following detailed description of the embodiments thereof, taken together with the drawings, in which:

DETAILED DESCRIPTION OF EMBODIMENTS

Overview

An embodiment of the present invention provides a receiver which receives a baseband signal at an input port of the receiver, and outputs a recovered baseband signal from an output port of the receiver. The input and output ports of the receiver are electrically insulated from each other, so that the receiver acts to electrically separate the input port and its incoming baseband signal from the output port and its outgoing recovered baseband signal.

The baseband signal received at the input port of the receiver is derived from electrical activity of tissue of a human patient. Typically the baseband signal comprises at least one of an electrocardiograph (ECG) signal and an electroencephalograph (EEG) signal, although the signal may be any other type of signal derived from a human patient, such as a signal generated by the patient's eye muscles.

The received baseband signal is modulated with a local oscillator (LO) signal in a modulator of the receiver, so as to generate a modulated LO signal. The modulation is typically amplitude modulation. The modulated LO signal is transferred to an isolating device, typically a transformer, so that the modulated LO signal is input to the primary coil of the transformer. The secondary coil of the transformer, galvanically insulated from the primary coil, generates a modulated output LO signal.

The modulated output LO signal is transferred to a demodulator, which also receives the LO signal. However, the LO signal to the demodulator is typically derived via an isolating transformer, so that the LO signal to the modulator and the LO signal to the demodulator may be referenced to separate reference rails which are electrically insulated from each other.

The demodulator demodulates the modulated output LO signal with the LO signal, thereby recovering the baseband signal, typically together with signals having other frequencies. The demodulator output may be filtered through a low pass filter to recover only the baseband signal.

The electrical isolation of the recovered baseband signal from the incoming baseband signal, and the isolation of ports at which the signals are present, considerably reduces any leakage current that may be generated in a patient connected to the receiver.

System Description

Figure 1:
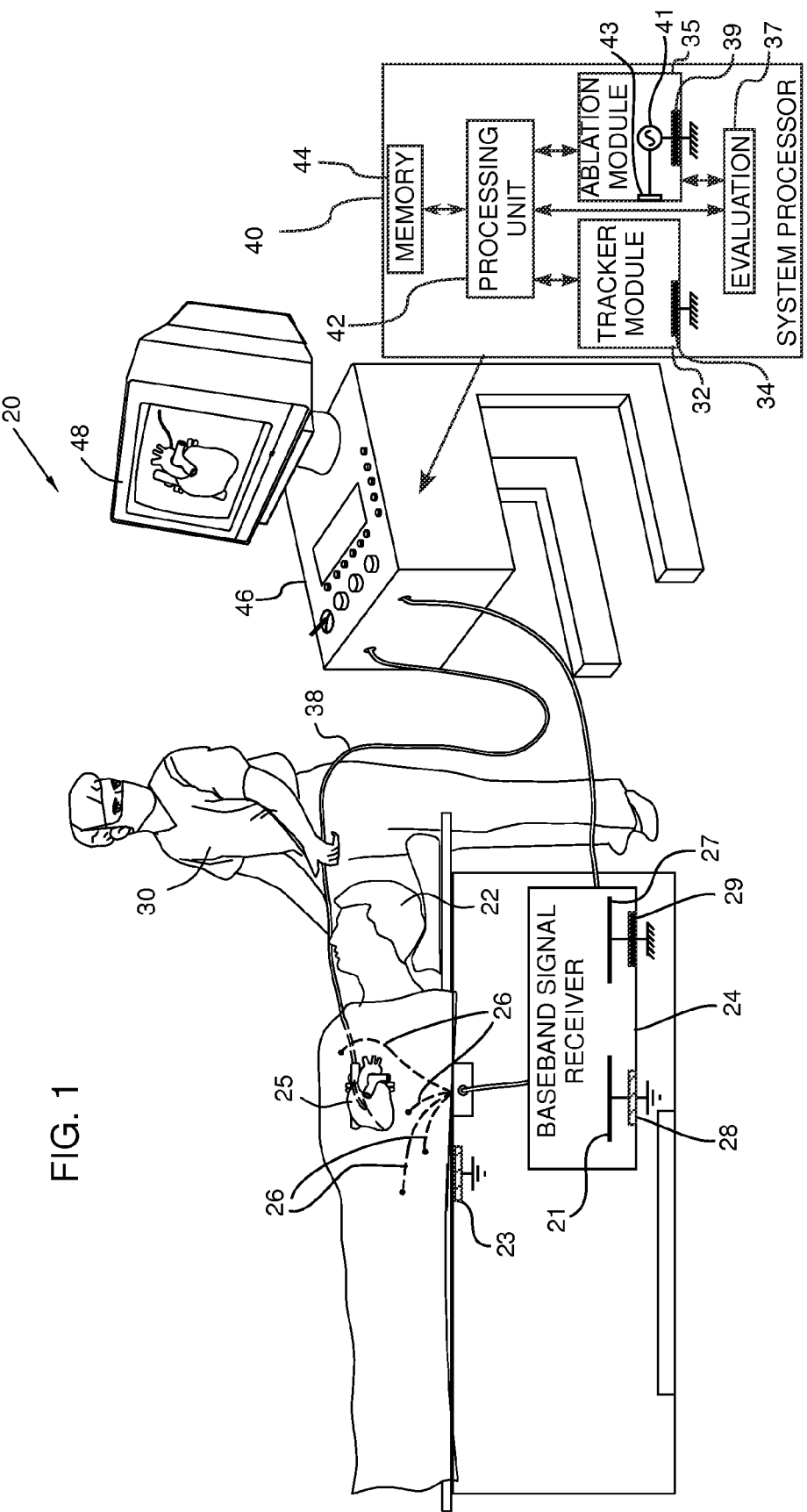
FIG. 1 is a schematic illustration of a system for measuring baseband signals, according to an embodiment of the present invention.

Reference is now made to FIG. 1, which is a schematic illustration of a system 20 for measuring baseband signals, according to an embodiment of the present invention. The baseband signals are assumed to be generated in response to electrical activity in tissue of the body of a human patient 22, and to comprise frequencies ranging from approximately 0 Hz to approximately 1 kHz. In addition to measuring the signals, system 20 insulates the patient from devices using the signals. Herein, by way of example, the baseband signals are assumed to comprise electrocardiograph (ECG) signals. However it will be understood that the baseband signals measured by embodiments of the present invention may comprise any baseband signals originating from patient 22, such as electroencephalograph (EEG) signals.

System 20 comprises a baseband signal receiver 24, which receives ECG signals generated by a heart 25 of patient 22, via leads 26 which are attached to the patient. A first reference rail 21 of receiver 24 is connected to a first receiver grounding electrode 28. Patient 22 is coupled to a patient grounding electrode 23, which is connected via electrode 28 to the first reference rail. Receiver 24 also comprises a second reference rail 27, which is connected to a second receiver grounding electrode 29. Characteristics of receiver 24, including characteristics of the first and second reference rails are described below.

Embodiments of the present invention may be used only for measurement of baseband signals, and in some cases only one such signal. For these embodiments only one piece of equipment, receiver 24, is galvanically connected to patient 22. Alternatively, other equipment, apart from receiver 24, may also be galvanically connected to patient 22. The other equipment may transmit electric signals to, or receive electric signals from, the patient. The signals of the other equipment may be baseband and/or non-baseband signals.

In the following description, a medical professional 30 is assumed to perform, by way of example, a procedure on patient 22, using a probe tracker module 32. Module 32 is connected (via receiver grounding electrode 29) to second reference rail 27 by a module grounding electrode 34. The tracker module typically tracks the location and orientation of a distal tip of a probe 38 within patient 22. In some cases module 32 tracks other sections of probe 38 within the patient. The tracker module may use any method for tracking probes known in the art. For example, module 32 may operate magnetic field transmitters in the vicinity of the patient, so that coils in probe 38 generate signals provided to the module, from which the location and orientation of the probe may be found. (For simplicity such transmitters are not shown in FIG. 1.) The Carto® system produced by Biosense Webster, of Diamond Bar, Calif., uses such a tracking method. Alternatively or additionally, tracker module 32 may track probe 38 by measuring impedances between one or more electrodes on the probe, and grounding electrode 23 and/or other electrodes (not shown) attached to the skin of patient 22. The Carto3® system produced by Biosense Webster uses both magnetic field transmitters and impedance measurements for tracking.

In addition to the tracking module, the procedure performed on patient 22 typically requires other equipment. For example, the procedure may include radiofrequency ablation, so that as well as tracker module 32 there is an ablation module 35 which provides ablation, as well as an evaluation module 37, which may be separate from the ablation module, for evaluating the level of ablation. Except where otherwise stated, ablation module 35 is assumed to be connected to the second reference rail by an ablation grounding electrode 39. A radiofrequency oscillator 41 comprised in the module provides radiofrequency power for the ablation at a power output port 43 of the module.

Except where otherwise stated, in the description hereinbelow the only other equipment assumed to be used during the procedure and connected to the patient (apart from receiver 24) is assumed to be tracker module 32.

System 20 and the other equipment, including tracker module 32, may be controlled by a system processor 40, comprising a processing unit 42 communicating with a memory 44. Processor 40 is typically mounted in a console 46, which comprises operating controls that professional uses to interact with the processor. The processor uses software stored in memory 44 to operate system 20. Results of the operations performed by processor 40 are presented to the professional on a screen 48, which typically displays a graphic user interface to the operator, and/or an image of the tissue undergoing the procedure. The software may be downloaded to processor 40 in electronic form, over a network, for example, or it may, alternatively or additionally, be provided and/or stored on non-transitory tangible media, such as magnetic, optical, or electronic memory.

Figure 2:
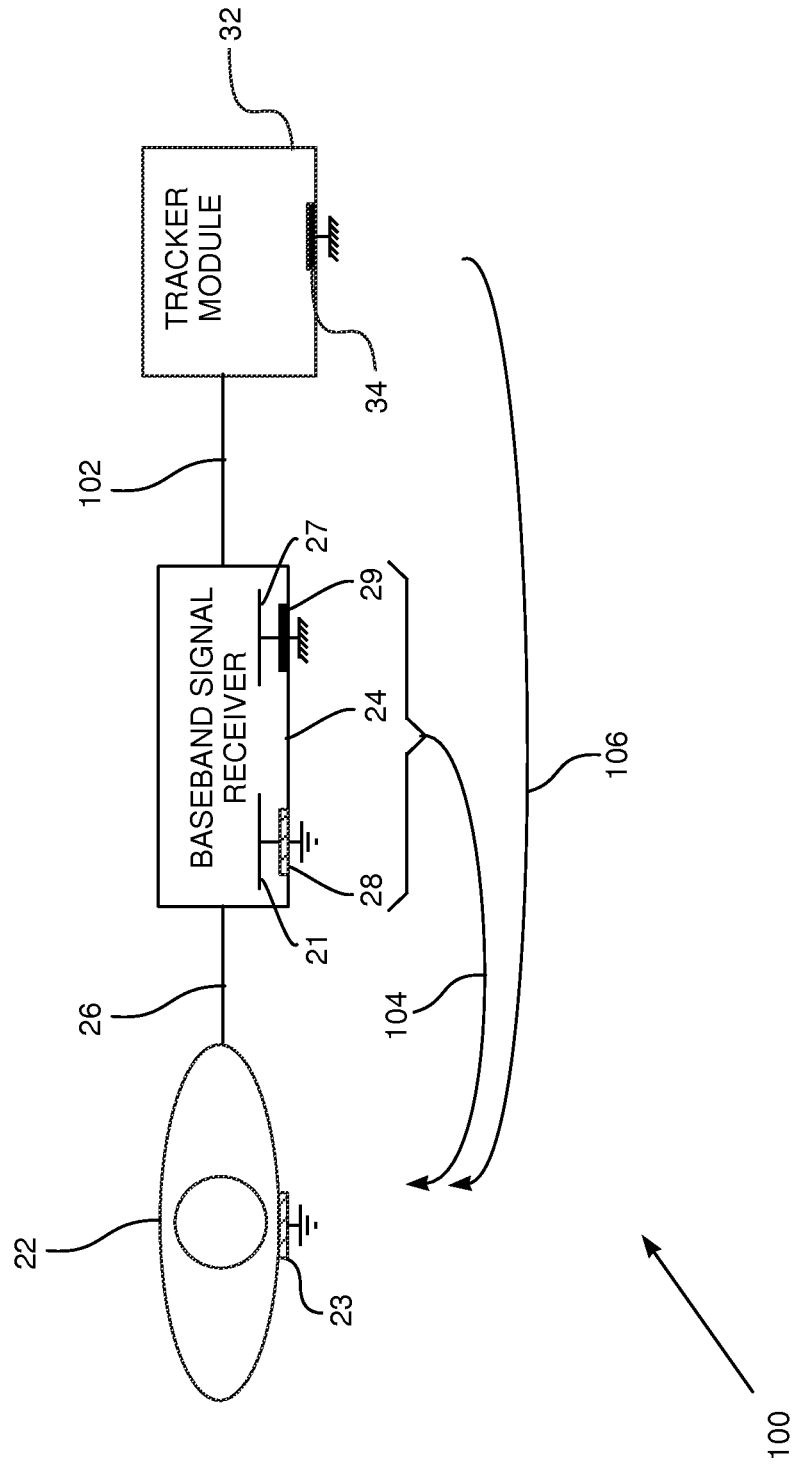
FIG. 2 is a schematic diagram illustrating properties of the system, according to an embodiment of the present invention.

FIG. 2 is a schematic diagram 100 illustrating properties of system 20, according to an embodiment of the present invention. As illustrated in diagram 100 by their corresponding symbols, grounding electrode 23 of the patient and grounding electrode 28 of the receiver are connected to first reference rail 21. In addition, grounding electrode 29 of the receiver, and grounding electrode 34 of the tracker module are connected to second reference rail 27. Tracker module 32 is assumed to use signals from receiver 24 via a connection 102. Such a use occurs, for example, when the tracker module gates location data of probe 38 according to ECG signals.

As shown by arrows 104 and 106, there are possible return current paths via electrode 23 from both receiver 24 and module 32 through patient 22. The actual currents flowing in each of the paths are at least partially dependent on the insulation between the first and second reference rails, so that the lower the insulation, the higher the current in the paths. The multiple currents through ground 23 may result in a leakage current through the patient that is larger than acceptable, even though receiver 24 and module 32 do not individually exceed their specified leakage ratings. (Typically, leakage requirements of receiver 24 and module 32 are prescribed by an IEC60601 standard published by the International Electrotechnical Commission, Geneva, Switzerland.) By ensuring that the insulation between the first and second reference rails, and respective components coupled to the two rails, is sufficiently high, embodiments of the present invention overcome this problem.

Figure 3:
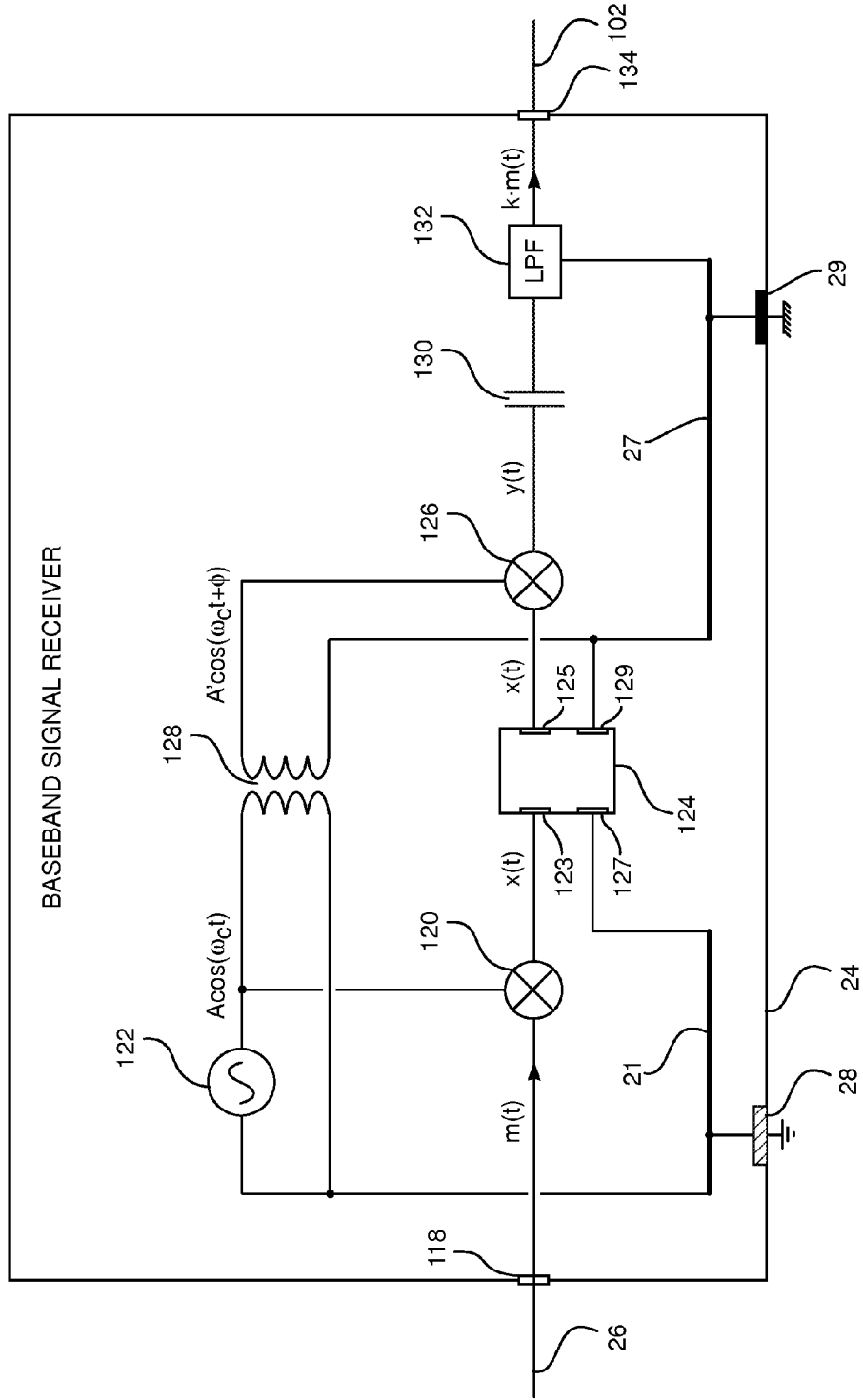
FIG. 3 is a schematic circuit diagram of a receiver, according to an embodiment of the present invention.

FIG. 3 is a schematic circuit diagram of receiver 24, according to an embodiment of the present invention. In some embodiments two or more leads 26 are connected to the receiver, and the respective signals from the leads are multiplexed. The multiplexed signal is transferred through the elements of receiver 24, and is demultiplexed into respective output signals. For simplicity, the diagram only shows one incoming lead 26 having one baseband signal, and those with ordinary skill in the art will be able to adapt the explanation herein for multiple incoming leads 26, and for the associated multiplexing and demultiplexing.

Lead 26 is connected to an input port 118 of the receiver, which in turn conveys an input baseband signal m(t) to a modulator 120. A local oscillator 122, which in some embodiments may be incorporated in the receiver, generates a local oscillator signal, $A \cdot \cos(\omega_c t)$, referenced to rail 21. Typically, the local oscillator signal has a frequency $\omega_c$ of the order of hundreds of kHz. In the following description, for simplicity, the local oscillator is assumed to oscillate at approximately 500 kHz. The local oscillator signal, also termed herein the carrier signal, has an amplitude A and a frequency $\omega_c$, and it is input to modulator 120 (the carrier phase is assumed to be 0). Signal m(t) modulates the carrier, generating an amplitude modulated signal x(t) at the modulator output given by equation (1):

$$x(t) = (C + m(t)) \cdot \cos(\omega_c t) \qquad (1)$$

where C is a number related to the amplitude A of the carrier.

Signal x(t) is an amplitude modulated signal having a frequency of the local oscillator, i.e., approximately 500 kHz. Signal x(t) is transferred to an input port 123 of an isolation device 124, the signal being referenced to reference rail 21 via an input grounding port 127 of the isolation device. As described below with regard to FIG. 4, a signal substantially the same as x(t) is generated at an output port 125 of device 124. The signal at output port 125 is referenced to reference rail 27 via an output grounding port 129 of isolation device 124. Examples of isolation device 124 are described below with respect to FIG. 4.

Figure 4:
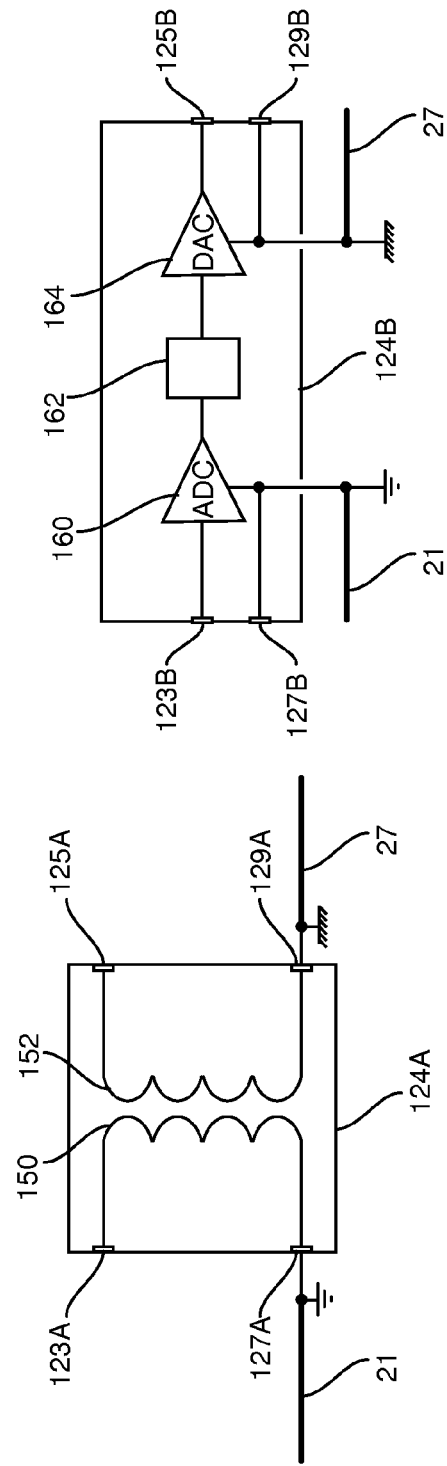
FIG. 4 illustrates examples of an isolation device, according to an embodiment of the present invention.

FIG. 4 illustrates examples of isolation device 124, according to an embodiment of the present invention. In the description of the examples, the devices are differentiated by having a suffix letter applied to the devices and their component parts, where these are common to the devices. Thus device 124A has an input port 123A, and device 124B has an input port 123B.

Isolation device 124A comprises a transformer having a primary coil 150 and a secondary coil 152. The two coils are galvanically insulated from each other. Primary coil 150 has a first primary coil termination which acts as input port 123A, and a second primary coil termination which acts as input grounding port 127A. Secondary coil 152 has a first secondary coil termination which acts as output port 125A, and a second secondary coil termination which acts as output grounding port 129A. As is illustrated in the diagram, input grounding port 127A is connected to reference rail 21, and output grounding port 129A is connected to reference rail 27. If, by way of example, the number of turns on primary coil 150 is the same as the number on secondary coil 152, then an output signal between output ports 125A and 129A is substantially the same as the input signal between input ports 123A and 127A.

As explained above, the input signal to device 124A is an amplitude modulated signal having the frequency of the local oscillator, assumed by way of example to be approximately 500 kHz. Typically, device 124A is configured to transfer these radio-frequencies, but to reject other frequencies, so that the device acts as a band-pass filter for radio-frequencies at the frequency of the local oscillator. Thus device 124A effectively blocks lower frequencies, such as the 50 Hz or 60 Hz signals that typically comprise leakage currents from patient 22.

Isolation device 124B comprises an analog to digital converter (ADC) 160, and a digital to analog converter (DAC) 164. An optoelectronic isolator 162 connects the digital output of ADC 160 to the digital input of DAC 164. The input to ADC 160 is across input port 123B and input grounding port 127B, the input grounding port being connected to reference rail 21. The output from DAC 164 is across output port 125B and output grounding port 129B, the output grounding port being connected to reference rail 27. Optoelectronic isolator 162 ensures that the input and output ports of device 124B are galvanically insulated from each other. As for device 124A, the output signal between output ports 125B and 129B is substantially the same as the input signal between input ports 123B and 127B.

As for device 124A, isolation device 124B may be configured as a band-pass filter, passing signals having frequencies close to the local oscillator frequency, and rejecting frequencies lower and higher than this frequency.

Returning to FIG. 3, for clarity the signal between input ports 123 and 127 is referred to as the primary signal of isolation device 124, and the signal between output ports 125 and 129 is referred to as the secondary signal of the isolation device. As explained above, isolation device 124 may be configured as a band-pass filter, passing a band of frequencies around the frequency of local oscillator 122, and rejecting frequencies outside this band. (Furthermore, between input port 123 and output port 125, and also between rails 21 and 27, there is a high electrical DC resistance, typically of the order of gigaohms or even teraohms.) The secondary signal from output ports 125 and 129 is input to a demodulator 126.

Demodulator 126 also receives, via an isolation transformer 128, a local oscillator, or carrier, signal $A' \cdot \cos(\omega_c t + \phi)$, from local oscillator 122. (A' represents the amplitude of the carrier signal output from the secondary of transformer 128; $\phi$ represents the phase difference between the signal output by transformer 128 and the signal input to the transformer.) Transformer 128 is substantially similar to isolation device 124A (FIG. 4), having a primary coil and a secondary coil that are galvanically insulated from each other. As shown in FIG. 3, (and as described for device 124A), an input grounding port of the primary coil of transformer 128 is connected to rail 21, and an output grounding port of the secondary coil of transformer 128 is connected to rail 27.

Demodulator 126 multiplies its two input signals to give an output signal y(t) that is referenced to rail 27. An expression for y(t) is given by equation (2):

$$y(t) = (C + m(t)) \cdot \cos(\omega_c t) \cdot A' \cdot \cos(\omega_c T + \phi) \quad (2)$$

Equation (2) may be rewritten:

$$y(t) = A' \cdot (C + m(t))[\cos(\omega_c t) \cdot \cos(\omega_c t + \varphi)] \quad (3)$$

$$= A' \cdot (C + m(t)) \frac{1}{2} [\cos(\varphi) + \cos(2\omega_c t + \varphi)]$$

Equation (3) may be further rewritten to show the expression for y(t) as three separate terms:

$$Y(t) = \quad (4)$$
$$\frac{1}{2} A' \cdot C \cos(\varphi) + \frac{1}{2} A' \cdot \cos(\varphi) m(t) + \frac{1}{2} A' \cdot (C + m(t)) \cos(2\omega_c t + \varphi)$$

where A', C. and $\phi$, defined above, have constant values.

Inspection of equation (4) shows that:

the first term on the right side of the equation, $$\frac{1}{2} A' \cdot C \cos(\varphi),$$

comprises only constant values. The first term represents a DC component of y(t);

the third term on the right side of the equation, $$\frac{1}{2} A' \cdot (C + m(t)) \cos(2\omega_c t + \varphi),$$

has a frequency component that is double the carrier frequency $\omega_c$; and the second term, $$\frac{1}{2} A' \cdot \cos(\varphi) m(t),$$

is a function of constant terms A' and $\phi$, and of baseband signal m(t).

The values given by all three terms are referenced to rail 27.

The second term may be rewritten using the identity equation (5):

$$\frac{1}{2} A' \cdot \cos(\varphi) m(t) \equiv k \cdot m(t) \quad (5)$$

where $k$ is a constant equal to $\frac{1}{2} A' \cdot \cos(\varphi)$.

Typically, a high value capacitor 130 filters out the DC component of y(t), i.e. the first term of equation (4); in one embodiment capacitor 130 is of the order of 1,000 μF. Alternatively, the DC component is filtered by other systems known in the art, including, but not limited to, one or more other electronic devices. A low pass filter (LPF) 132 is configured to allow baseband frequencies to pass, but to reject higher frequencies such as those represented by the third term. Because the third term has significantly higher frequencies (of the order of 1 MHz) than the baseband frequencies, LPF 132 can be efficiently configured to pass baseband frequencies, i.e., up to 1 kHz, and reject higher frequencies such as third term frequencies. Filter 132 thus only passes signals k·m(t), i.e., signals having levels that are a direct function of input signal m(t), and so that have only baseband frequencies. Signals k·m(t) are output from an output port 134 of the receiver. If, as illustrated above in FIG. 2, receiver 24 is connected to tracker module 32 via connection 102, signals k·m(t) transmit on the connection.

As explained above with reference to equation (5), k is a constant. As will be apparent to those having ordinary skill in the art, a value of k for a given receiver 24 may be evaluated by inputting a known baseband signal into port 118, and comparing the known signal with the output signal generated at port 134.

The value of k may be stored in memory 44 and used as required by processing unit 42. Alternatively or additionally, the value of k may be stored in a dedicated memory of receiver 24, and used by a dedicated processor of the receiver, in order to generate a value of m(t) at output port 134. For simplicity, neither a receiver dedicated memory nor a receiver dedicated processor are shown in the diagrams.

Consideration of FIG. 3, and of the description above, shows that in addition to receiver 24 measuring the baseband signals received from patient 22, the receiver also acts as an electrical "separator," since a front end of the receiver, comprising input port 118, is electrically insulated from part of the rest of the receiver, comprising output port 134. Examples of the use of the receiver as an electrical separator, where it is not directly connected to patient 22, are provided below with reference to FIGS. 6, 7, and 8.

Figure 5:
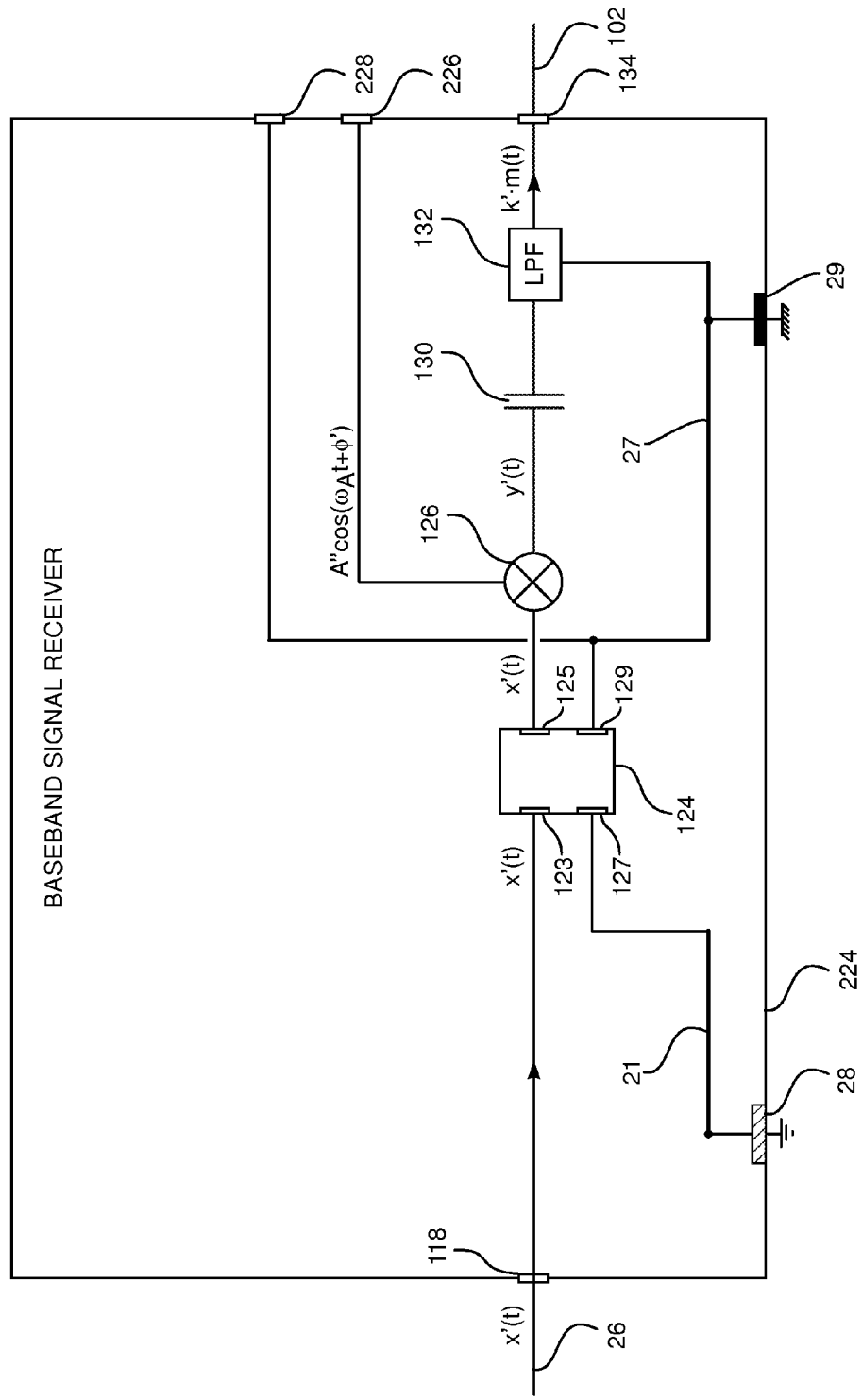
FIG. 5 is a schematic circuit diagram of a receiver, according to an alternative embodiment of the present invention.

FIG. 5 is a schematic circuit diagram of a receiver 224, according to an alternative embodiment of the present invention. Apart from the differences described below, the operation of receiver 224 is generally similar to that of receiver 24 (FIGS. 1-4), and elements indicated by the same reference numerals in both receivers 24 and 224 are generally similar in construction and in operation. Unlike receiver 24, receiver 224 does not comprise a local oscillator 122, an isolating transformer 128, or a modulator 120. Also unlike receiver 24, receiver 224 does not receive a baseband signal m(t) at input port 118.

Rather, receiver 224 receives at input port 118 a carrier signal that has been modulated by baseband signal m(t). This type of modulated carrier signal occurs, for example, during radiofrequency ablation of tissue of patient 22. In the following description, patient 22 is assumed to be ablated using ablation module 35 (FIG. 1). The radiofrequency ablation from the module is implemented using oscillator 41, which is assumed to provide a frequency $\omega_A$ that is approximately the same as the frequency $\omega_c$ provided by local oscillator 122. The radiofrequency ablation power from the oscillator is applied to patient 22 via one or more electrodes (not shown in FIG. 1) in probe 38. The application of the radiofrequency power to the tissue of the patient causes the baseband signals (generated in response to electrical activity in tissue of patient 22) to modulate an ablation frequency signal.

The modulated ablation frequency signal appears in leads 26, and is herein represented as x'(t), to correspond with modulated signal x(t) of receiver 24. An expression for x'(t), corresponding to equation (1), is given by equation (6):

$$x'(t)=(C'+m(t))\cdot\cos(\omega_A t) \quad (6)$$

where C' is a number related to the amplitude of the ablation power applied to patient 22.

In FIG. 5 and in the following description parameters y'(t), A", φ', and k' of receiver 224 respectively correspond with parameters y, A', φ, and k of receiver 24.

An input grounding port 228 of receiver 224 is connected to rail 27, and the port is also connected to ablation module grounding electrode 39. Thus signals from the ablation module are referenced to rail 27. Demodulator 126 receives from an input carrier signal port 226 a carrier signal A"·cos($\omega_A t$+φ'), derived, typically using attenuation, from power output port 43. As described above for receiver 24, a signal y'(t) from demodulator 128 passes to capacitor 130, and a signal k'·m(t), substantially similar to k·m(t), is output at port 134.

In receiver 224 a value for k' may be determined in generally the same manner as is described above for evaluating parameter k. Typically, for receiver 224 the value of k' may be found by simulating an ablation procedure, using simulated tissue and applying a known simulated baseband signal to the simulated tissue.

The disclosure above describes a number of different configurations in which one baseband signal receiver 24 or 224 may be connected to patient 22. It will be understood that these configurations are for the purpose of exemplification, and other configurations will be apparent to those having ordinary skill in the art. Such configurations include, but are not limited to, configurations where the output of the baseband signal receiver is applied simultaneously to multiple different modules such as tracker module 32, ablation module 35, and evaluation module 37.

Figure 6:
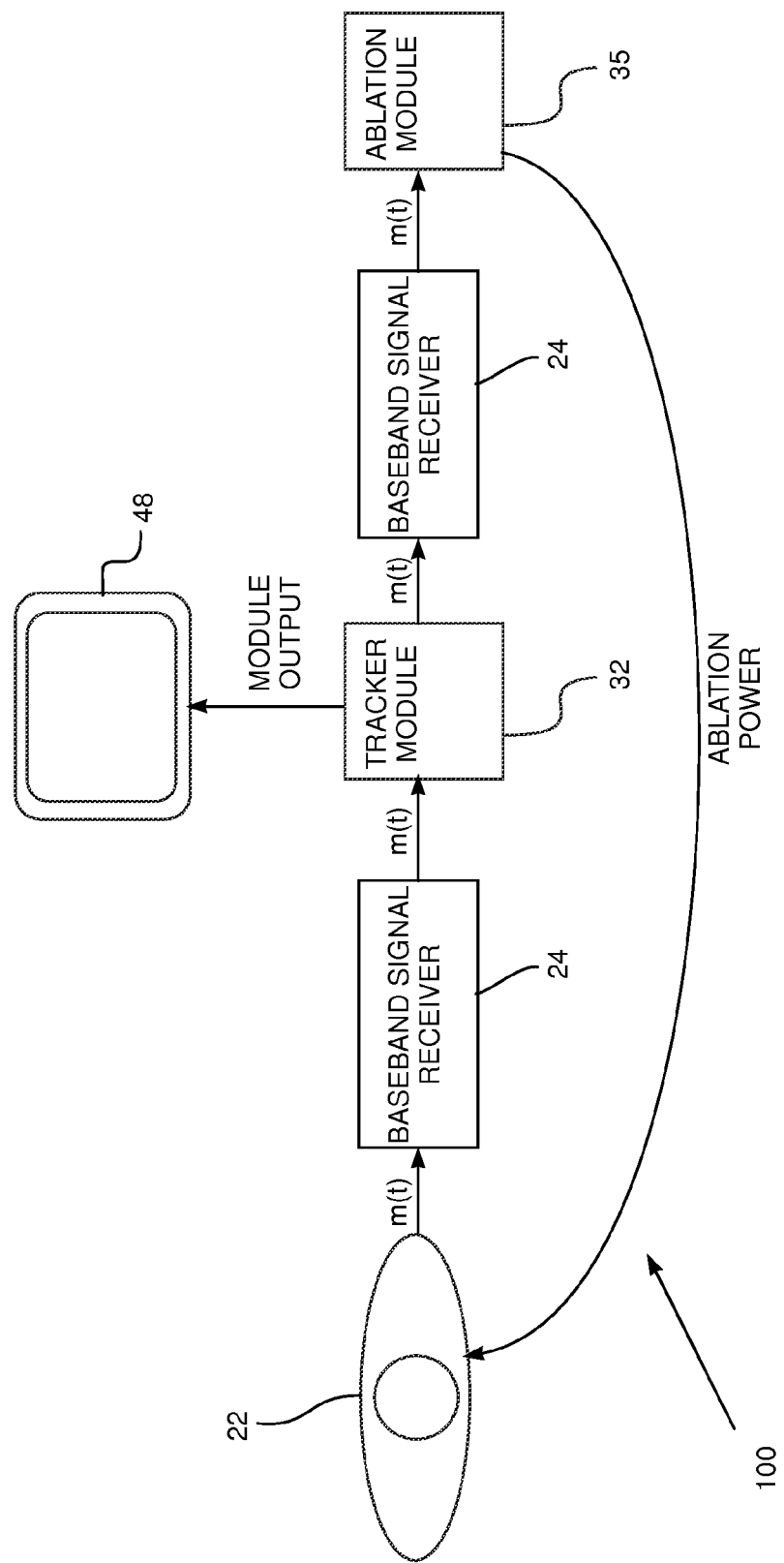
FIG. 6 is a schematic diagram illustrating the connection of two baseband signal receivers in series, according to an embodiment of the present invention.

It will further be understood that the electrical isolation or separation achieved by one baseband signal receiver may be enhanced by connecting two or more baseband signal receivers in series, for example in series with modules such as tracker module 32 and ablation module 35. In this case a first receiver may be connected between the patient and a first module, and a second receiver may be connected between the first module and the second module. FIG. 6 illustrates such a configuration.

FIG. 6 is a schematic diagram illustrating the connection of two baseband signal receivers in series, according to an embodiment of the present invention. As is shown in the diagram, in an arrangement 100 a first receiver 24 is connected between patient 22 and tracker module 32, so as to provide isolated baseband signals to the tracker module, substantially as described above with reference to FIGS. 1-4. Module 32 provides its tracker output to screen 48. In addition tracker module 32 conveys a baseband signal to a second receiver 24, which provides isolated baseband signals to ablation module 35. (Ablation module 35 may use the baseband signals, for example, to determine a level of ablation power to be applied to patient 22 by the ablation module.) Typically, ablation module 35 may have its grounding electrode 39 disconnected from rail 27, so that the two modules are completely isolated. In summary, first receiver 24 isolates tracker module 32 from patient 22, and second receiver 24 isolates tracker module 32 from ablation module 35.

Figure 7:
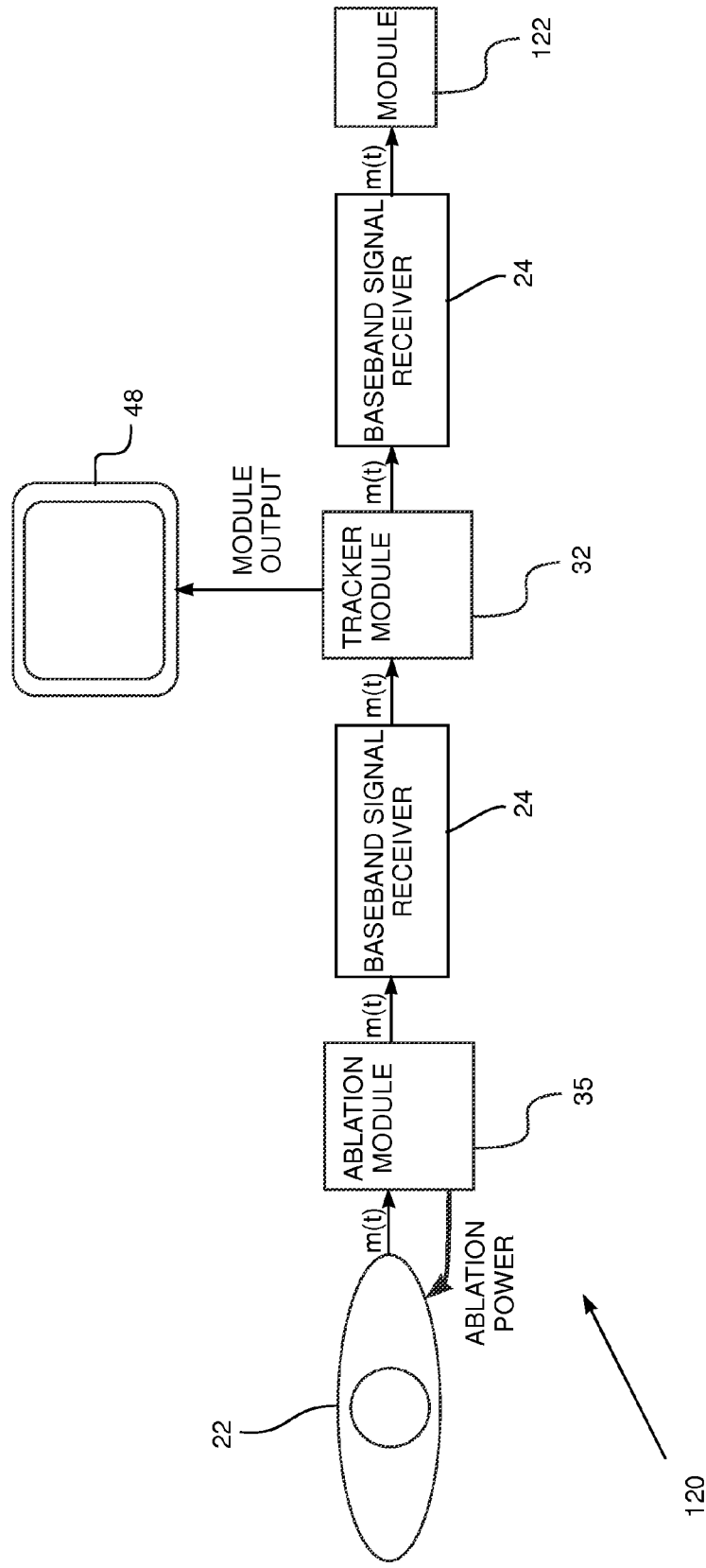
FIG. 7 is a schematic diagram illustrating an alternative arrangement of two baseband signal receivers in series, according to an embodiment of the present invention.

FIG. 7 is a schematic diagram illustrating an alternative arrangement 120 of the modules in arrangement 100, according to an embodiment of the present invention. In arrangement 120 ablation module 35 is directly connected to patient 22. The baseband signal is derived from the ablation module, and is transferred via a first receiver 24 to the tracker module, so that the first receiver acts to isolate and separate the ablation module from the tracker module. Arrangement 120 illustrates that a second receiver 24 transfers the baseband signal to a third module 122, which may be any module, such as an EEG recorder, that is used during the procedure being performed on patient 22.

The second receiver 24 isolates module 122 from any previous modules, such as tracker module 32. It will be understood that the arrangement illustrated in FIG. 7 may be extended for any number of modules, by positioning receivers 24 between adjacent modules. Each receiver 24 acts to isolate and separate the modules to which it is connected.

Figure 8:
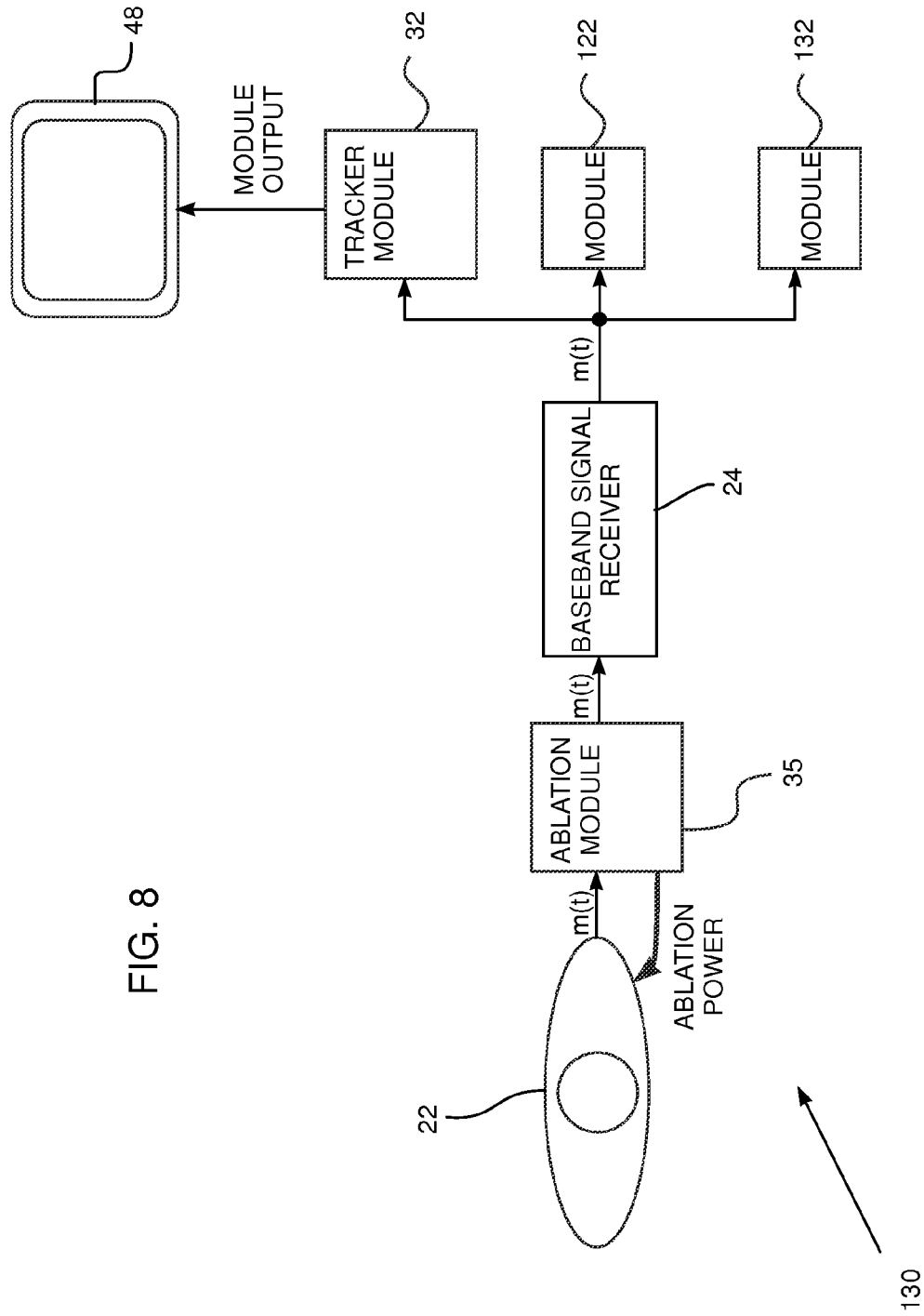
FIG. 8 is a schematic diagram illustrating a baseband signal receiver connected to a number of modules, according to an embodiment of the present invention.

FIG. 8 is a schematic diagram illustrating a further alternative arrangement 130 of the modules in arrangements 100 and 120, according to an embodiment of the present invention. In arrangement 130 ablation module 35 is directly connected to patient 22, and is separated from all subsequent modules by a single receiver 24. As described above, receiver 24 transfers its incoming baseband signals to the subsequent modules. By way of example the subsequent modules are assumed to be tracker module 32, module 122, and a further module 132, such as an EEG alarm. As illustrated in the figure, the subsequent modules all receive the baseband signals from the output of the single receiver 24, and so all are isolated from ablation module 35.

Arrangements using one or more receivers 24 as isolating receivers, other than those exemplified above, will be apparent to those having ordinary skill in the art, and all such arrangements are assumed to be included within the scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A baseband receiver, comprising:
a receiver input port, configured to receive a baseband signal generated in response to electrical activity in tissue of a human patient;
a modulator, configured to modulate a local oscillator signal with the baseband signal;
an isolating device configured to receive the modulated local oscillator signal at an input port of the device and in response to generate a modulated output local oscillator signal at an output port of the device;
an input reference rail;
an output reference rail, the input reference rail and the output reference rail being different and electrically insulated from each other, the received baseband signal is referenced to the input reference rail; and
a demodulator configured to demodulate the modulated output local oscillator signal with the local oscillator signal so as to recover the baseband signal, the recovered baseband signal is referenced to the output reference rail.

2. The receiver according to claim 1, wherein the isolating device comprises a transformer having a primary coil galvanically insulated from a secondary coil.

3. The receiver according to claim 1, wherein the isolating device comprises an optoelectronic converter having an input port galvanically insulated from an output port.

4. The receiver according to claim 3, further comprising an analog to digital converter (ADC) coupled to the input port, and a digital to analog converter (DAC) coupled to the output port, and wherein the ADC and the DAC are connected to the optoelectronic converter.

5. The receiver according to claim 1, further comprising a local oscillator configured to generate the local oscillator signal.

6. The receiver according to claim 5, wherein the local oscillator signal modulated by the modulator is referenced to the input reference rail.

7. The receiver according to claim 5, wherein the local oscillator signal is input to the demodulator, and is referenced to the output reference rail.

8. The receiver according to claim 1, further comprising an isolating transformer configured to electrically insulate the local oscillator signal input to the modulator from the local oscillator signal input to the demodulator.

9. The receiver according to claim 1, further comprising a low pass filter coupled to the demodulator and configured to reject frequencies higher than baseband frequencies.

10. The receiver according to claim 1, further comprising a processor configured to store a parameter relating the baseband signal received at the receiver input port with the recovered baseband signal from the demodulator.

11. The receiver according to claim 1, further comprising a receiver output port configured to receive the recovered baseband signal from the demodulator, and to provide the recovered baseband signal to a module configured to perform at least one of an electrical signal transmission to the human patient and an electrical signal reception from the human patient.

12. The receiver according to claim 11, wherein the module comprises a tracker module configured to receive tracking signals from the human patient so as to track a probe within the patient.

13. The receiver according to claim 11, wherein the module comprises an ablation module configured to transmit ablation power to the human patient so as to ablate the tissue.

14. The receiver according to claim 1, further comprising an electronic device coupled to the demodulator and configured to reject a direct current (DC) level.

15. A baseband receiver, comprising:
an isolating device configured to receive a local oscillator signal modulated by a baseband signal, generated in response to electrical activity in tissue of a human patient, at an input port of the device and in response to generate a modulated output local oscillator signal at an output port of the device;
an input reference rail;
an output reference rail, the input reference rail and the output reference rail being different and electrically insulated from each other, the received baseband signal is referenced to the input reference rail; and
a demodulator configured to demodulate the modulated output local oscillator signal with the local oscillator signal so as to recover the baseband signal, the recovered baseband signal is referenced to the output reference rail.

16. The receiver according to claim 15, wherein the isolating device comprises a transformer having a primary coil galvanically insulated from a secondary coil.

17. The receiver according to claim 15, further comprising an ablation module configured to transmit ablation power to the human patient at an ablation frequency, the module comprising a local oscillator configured to provide the local oscillator signal to the demodulator at the ablation frequency.

18. A method, comprising:
receiving a baseband signal generated in response to electrical activity in tissue of a human patient, the baseband signal being referenced to an input reference rail;
modulating a local oscillator signal with the baseband signal;
receiving the modulated local oscillator signal at an input port of an isolating device and in response generating a modulated output local oscillator signal at an output port of the device; and
demodulating the modulated output local oscillator signal with the local oscillator signal so as to recover the baseband signal, the recovered baseband signal being referenced to an output reference rail, the input reference rail and the output reference rail being electrically insulated from each other.

19. The method according to claim 18, wherein the isolating device comprises a transformer having a primary coil galvanically insulated from a secondary coil.

20. The method according to claim 18, wherein the isolating device comprises an optoelectronic converter having an input port galvanically insulated from an output port.

21. The method according to claim 18, wherein the local oscillator signal modulating the baseband signal is referenced to the input reference rail.

22. The method according to claim 18, wherein the local oscillator signal demodulating the modulated output local oscillator signal is referenced to the output reference rail.

23. The method according to claim 18, further comprising electrically insulating the local oscillator signal modulating the baseband signal from the local oscillator signal demodulating the modulated output local oscillator signal.

24. The method according to claim 18, further comprising storing a parameter relating the received baseband signal with the recovered baseband signal.

25. The method according to claim 18, further comprising providing the recovered baseband signal to a module configured to perform at least one of an electrical signal transmission to the human patient and an electrical signal reception from the human patient.

26. The method according to claim 25, wherein the module comprises a tracker module configured to receive tracking signals from the human patient so as to track a probe within the patient.

27. The method according to claim 25, wherein the module comprises an ablation module configured to transmit ablation power to the human patient so as to ablate the tissue.

28. A method, comprising:
receiving a local oscillator signal modulated by a baseband signal, generated in response to electrical activity in tissue of a human patient, at an input port of an isolating device and in response generating a modulated output local oscillator signal at an output port of the device, the baseband signal being referenced to an input reference rail; and
demodulating the modulated output local oscillator signal with the local oscillator signal so as to recover the baseband signal, the recovered baseband signal being referenced to an output reference rail, the input reference rail and the output reference rail being electrically insulated from each other.

29. The method according to claim 28, wherein the isolating device comprises a transformer having a primary coil galvanically insulated from a secondary coil.

30. The method according to claim 28, further comprising transmitting ablation power to the human patient at an ablation frequency from an ablation module, the module comprising a local oscillator configured to provide the local oscillator signal for demodulating the modulated output local oscillator signal at the ablation frequency.

* * * * *